(12) United States Patent
Ciulla

(10) Patent No.: US 10,085,759 B2
(45) Date of Patent: Oct. 2, 2018

(54) KIDNEY STONE SUCTION DEVICE

(71) Applicant: Boston Scientific Scimed, Inc., Maple Grove, MN (US)

(72) Inventor: Ronald Ciulla, Westford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 316 days.

(21) Appl. No.: 14/816,540

(22) Filed: Aug. 3, 2015

(65) Prior Publication Data

US 2016/0045208 A1    Feb. 18, 2016

Related U.S. Application Data

(60) Provisional application No. 62/037,456, filed on Aug. 14, 2014.

(51) Int. Cl.
| | | |
|---|---|---|
| *A61B 17/22* | (2006.01) | |
| *A61M 1/00* | (2006.01) | |
| *A61B 17/221* | (2006.01) | |
| *A61B 17/00* | (2006.01) | |

(52) U.S. Cl.
CPC .......... *A61B 17/22* (2013.01); *A61B 17/221* (2013.01); *A61M 1/008* (2013.01); *A61B 2017/00296* (2013.01); *A61B 2017/22079* (2013.01); *A61B 2217/005* (2013.01)

(58) Field of Classification Search
CPC ............... A61B 17/221; A61B 17/22; A61B 2017/00296; A61B 2017/22079; A61B 2017/2215; A61B 2217/005; A61B 2017/22034; A61B 17/12109; A61B 17/12172; A61F 2/013; A61M 1/008
USPC .......................... 606/123, 127, 200
See application file for complete search history.

(56) References Cited

U.S. PATENT DOCUMENTS

| | | | | |
|---|---|---|---|---|
| 2002/0016564 | A1* | 2/2002 | Courtney | A61B 17/22 604/96.01 |
| 2005/0251199 | A1* | 11/2005 | Osborne | A61F 2/01 606/200 |
| 2006/0015136 | A1* | 1/2006 | Besselink | A61F 2/013 606/200 |
| 2009/0054803 | A1* | 2/2009 | Saadat | A61B 1/0008 600/546 |
| 2009/0299403 | A1* | 12/2009 | Chanduszko | A61F 2/01 606/200 |
| 2011/0264072 | A1* | 10/2011 | Kunis | A61B 17/3478 604/506 |

* cited by examiner

*Primary Examiner* — Katherine M Shi
(74) *Attorney, Agent, or Firm* — Bookoff McAndrews, PLLC

(57) ABSTRACT

A method of using a suction device to remove an object from a subject's body includes extending a suction device into the body through a lumen of a medical device and expanding the suction head from a contracted configuration to an expanded configuration within the body. The suction head may be provided at a distal end of an elongate conduit. The method may also include applying suction to move the object into the expanded suction head, and removing the suction device with the object from the body.

15 Claims, 5 Drawing Sheets

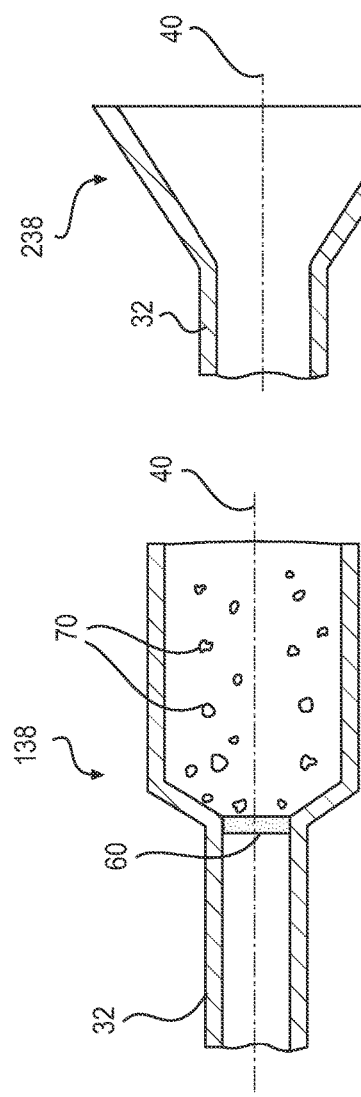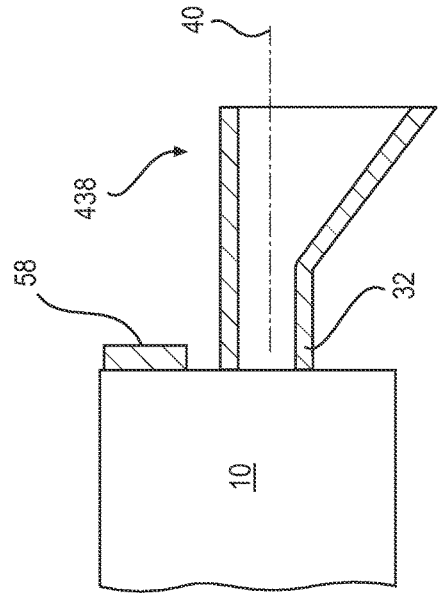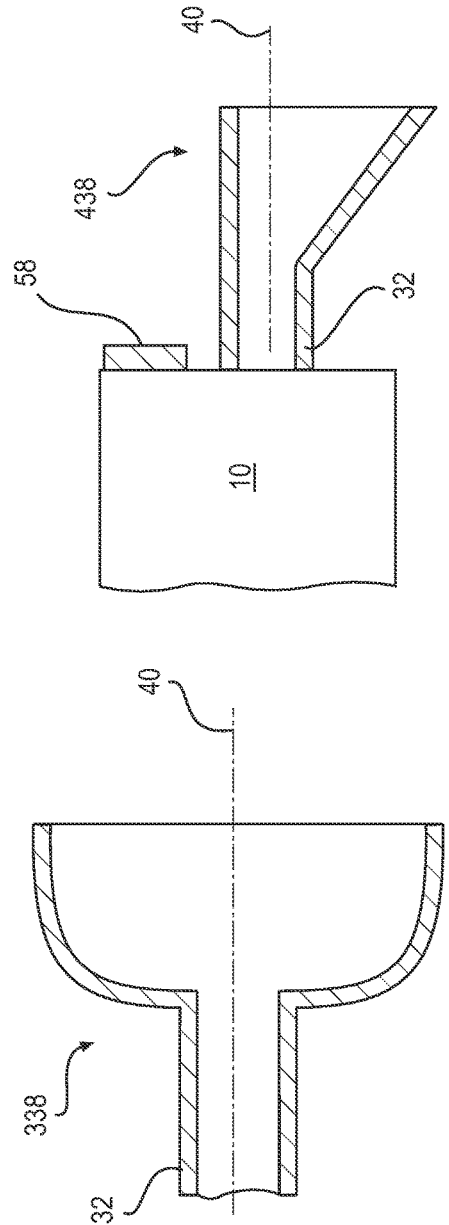

KIDNEY STONE SUCTION DEVICE

CROSS-REFERENCE TO RELATED APPLICATIONS

The application claims the benefits of priority from U.S. Provisional Application No. 62/037,456, filed on Aug. 14, 2014, which is incorporated by reference herein in its entirety.

TECHNICAL FIELD

Embodiments of the present disclosure relate generally to endoscopic suction devices and methods of using the suction devices. In particular, embodiments of the present disclosure relate to suction devices and methods for the extraction of stone fragments from the urinary tract of a patient.

BACKGROUND

Open surgical intervention was once the standard treatment for the removal of calculi or stones from the urinary tract of a patient. But other less invasive techniques, such as ureteroscopy, have emerged as safe and effective alternatives to open surgery. During ureteroscopy, the doctor inserts an ureteroscope into the urinary tract through a natural opening in the body and positions the scope proximate the kidney stone. The stone may then be captured and removed from the body using a small basket that extends into the urinary tract through the ureteroscope. While smaller stones may be removed in one piece, larger stones may need to be broken up (or fragmented) before they can be successfully removed. Many techniques, such as lithotripsy, exist to break up stones within the body.

Lithotripsy devices direct energy (electrohydraulic, ultrasonic, electromechanical, laser, etc.) through a probe to fragment the stone. These devices may be introduced into the body through the working lumen of the ureteroscope, or may be introduced percutaneously. In percutaneous endoscopic techniques, a lithotripsy device may be introduced into the body through a small puncture in the body. The device may be positioned proximate the stone and focused shock waves (or another energy) may be applied to the stone to break the stone into multiple fragments. The fragments may then be allowed to pass naturally out of the body or may be removed using a basket.

In some cases, it may be desirable to remove all the stone fragments from the body to prevent stone recurrence and stone migration. Larger stone fragments may be successfully removed using the basket. However, smaller fragments (typically less than 1 mm) may be difficult to remove using the basket. In some cases, a suction tube of the lithotripsy device may be used collect the smaller stone fragments. However, removal of stone fragments though the suction tube may result in clogging that necessitates repeated removal, cleaning and reinsertion of the tube during an operation. The methods and systems of the current disclosure may rectify some of the deficiencies described above.

SUMMARY OF THE DISCLOSURE

Embodiments of the present disclosure include medical devices, such as a suction tool, that may be used to remove material such as kidney stone from a patient's body, and methods of use thereof.

In one example, an endoscopic suction device is disclosed. The suction device may include an elongate conduit extending from a proximal end to a distal end along a longitudinal axis. The proximal end may be configured to be coupled to a vacuum source and the distal end may be configured to extend into a subject's body. The suction device may also include an expandable suction head at the distal end of the elongate conduit, the suction head may be configured to expand from a contracted configuration to an expanded configuration within the body.

Additionally or alternatively, the suction device may further include one or more of the following features: the distal end of the elongate conduit may be sized to extend into the body through a lumen of a medical device and the suction head may be configured to transform from a contracted configuration within the lumen to an expanded configuration outside the lumen; the lumen may be part of an ureteroscope; the suction head may be self-expandable; the suction head may include a shape-memory alloy; the device may further include an activation device configured to apply energy to the suction head to transform the suction head from the contracted configuration to the expanded configuration; suction head includes a filter; in the expanded configuration, a cross-sectional area of the suction head transverse to the longitudinal axis decreases from a distal-most end of the suction head to a proximal end of the suction head; a cross-sectional area of the suction head transverse to the longitudinal axis is greater in the expanded configuration than in the contracted configuration; the elongate conduit and the suction head may be formed as a single part; the elongate conduit and the suction head may be two parts attached together; the elongate conduit may include a flexible polymeric tube; the proximal end of the elongate conduit may include a handle; the proximal end of the elongate conduit may include a luer fitting adapted to connect the elongate conduit to the vacuum source; and in the expanded configuration, the suction head may have one of a wine glass shape, a conical shape, or a cylindrical shape.

In an additional or alternative example, method of using a suction device to remove an object from a subject's body is disclosed. The suction device may include an expandable suction head at a distal end of an elongate conduit. The method may include extending the suction device into the body through a lumen of a medical device and expanding the suction head from a contracted configuration to an expanded configuration within the body. The method may also include applying suction to move the object into the expanded suction head, and removing the suction device with the object from the body.

Additionally or alternatively, the method may include one or more of the following features: expanding the suction head may include transforming the suction head from a contracted configuration within the lumen to an expanded configuration outside the lumen; removing the suction device may include removing the suction device through the lumen; removing the suction device may include removing the lumen along with the suction device from the body; the suction head may be self-expandable.

In an additional or alternative example, method of removing a kidney stone from a subject's urinary tract is disclosed. The method may include inserting a medical device with a lumen into the urinary tract and extending a suction device into the urinary tract through the lumen. The suction device may include a self-expandable suction head at a distal end of an elongate conduit. The method may also include expanding the suction head from a contracted configuration within the lumen to an expanded configuration outside the lumen. The method may further include applying suction to move the stone into the expanded suction head, and removing the suction device with the stone from the urinary tract.

Alternatively or additionally, the method may further include one or more of the following features: inserting a medical device may include inserting a ureteroscope into the urinary tract; in the expanded configuration, a cross-sectional area of the suction head transverse to a longitudinal axis of the suction head may decrease from the distal-most end of the suction head to a proximal end of the suction head; removing the suction device may include removing the medical device along with the suction device from the urinary tract; a cross-sectional area of the suction head transverse to a longitudinal axis of the suction head may be greater in the expanded configuration than in the contracted configuration.

Additional objects and advantages of the present disclosure will be set forth in part in the description which follows, and in part will be understood from the description, or may be learned by practice of the claimed disclosure. The objects and advantages of the claimed disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 5A-5D illustrate some exemplary shapes of the suction head of the suction tool of FIG. 2;

DESCRIPTION OF THE EMBODIMENTS

Overview

The present disclosure is drawn to suction devices and related systems and methods. Specifically, the present disclosure is drawn to suction device for removing material from a body and methods of using the suction device in a medical procedure. The suction device may include an elongate conduit with an expandable head at its distal end. Reference will now be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

Exemplary Aspects

Figure 1:
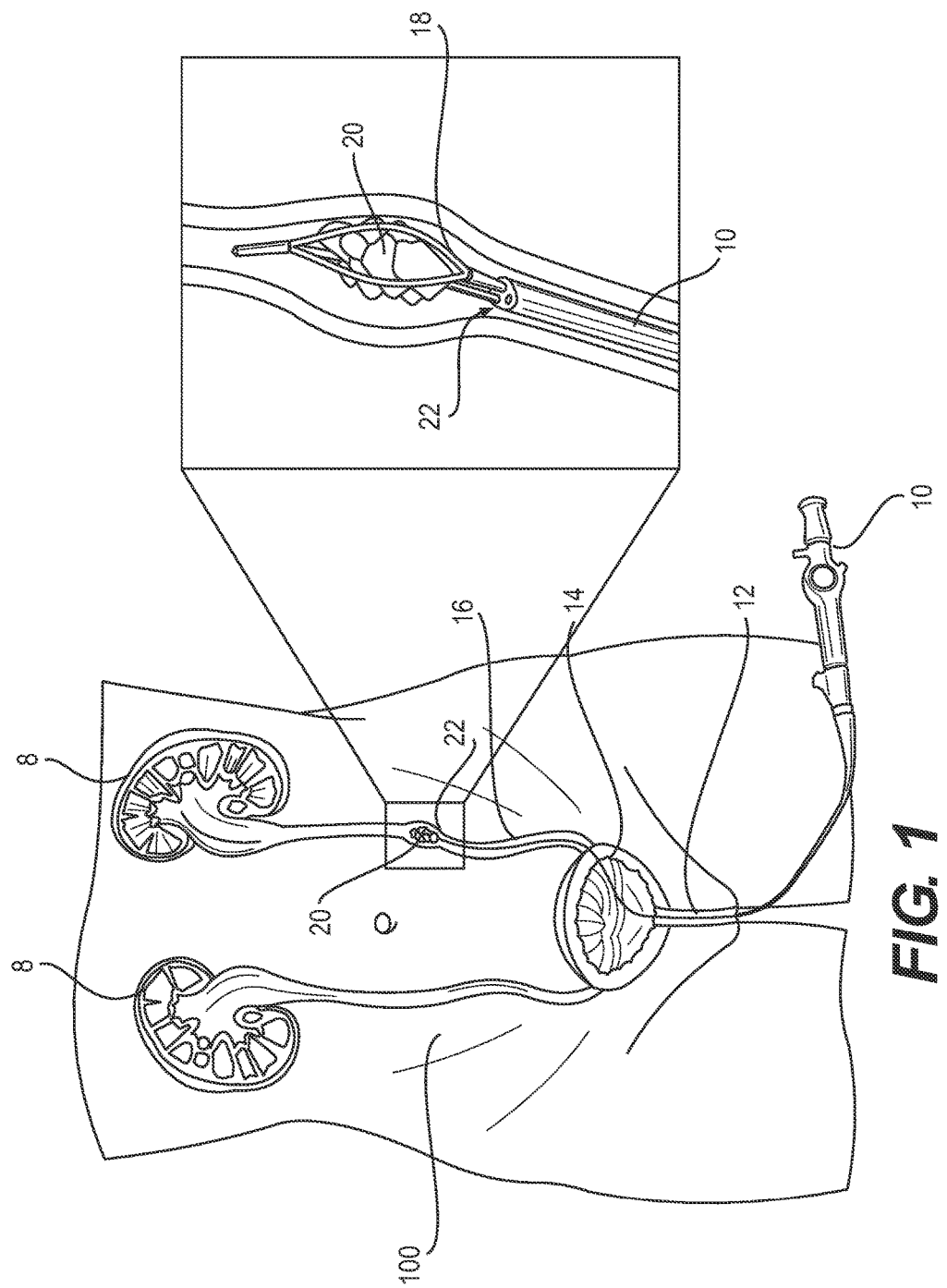
FIG. 1 illustrates the urinary tract of a female patient.

FIG. 1 illustrates the pelvic region of a female patient with a kidney stone 20 ("stone") embedded in a ureter 16 of the urinary tract 100. As known in the art, the urinary tract 100 includes a pair of kidneys 8, a pair of ureters 16, a bladder 14, and a urethra 12. Stones in the ureter 16 can cause extreme pain as the body attempts to push them through the ureter 16 into the bladder 14. In some cases, a doctor (typically a urologist) performs a procedure known as ureteroscopy to remove these stones 20 from the body. In this procedure, the doctor inserts a ureteroscope 10 (a thin flexible viewing instrument) into the body through the vagina, and pushes the ureteroscope 10 into the ureter 16, to position its distal end 22 proximate the stone 20. After the ureteroscope 10 is suitably positioned, a small basket 18 may be introduced into the ureter 16 through a lumen of the ureteroscope 10, and maneuvered to capture the stone 20 therein. The basket 18 along with the captured stone may then be removed from the body through the ureteroscope 10. Although FIG. 1 illustrates the stone 20 as being embedded in a ureter 16 (a medical condition referred to as ureterolithiasis), it should be noted the stone 20 may be located anywhere in the urinary tract 100.

If the stone 20 is too large to be removed as one piece using the basket 18, a known procedure (for example, lithotripsy, percutaneous nephrolithotomy (PCNL), etc.) may be used to break a large stone 20 into smaller fragments. Since procedures used to break stones into smaller fragments are known in the art, these techniques are not discussed herein. In some of these procedures, focused energy (ultrasonic energy, laser energy, etc.) may be used to break the stone 20 into smaller fragments. The larger of these fragments may be removed using basket 18. The smaller fragments, which may be too small to be removed using the basket 18, may be collected and removed from the body using a suction tool introduced into the ureter 16 through a lumen of the ureteroscope 10.

Figure 2:
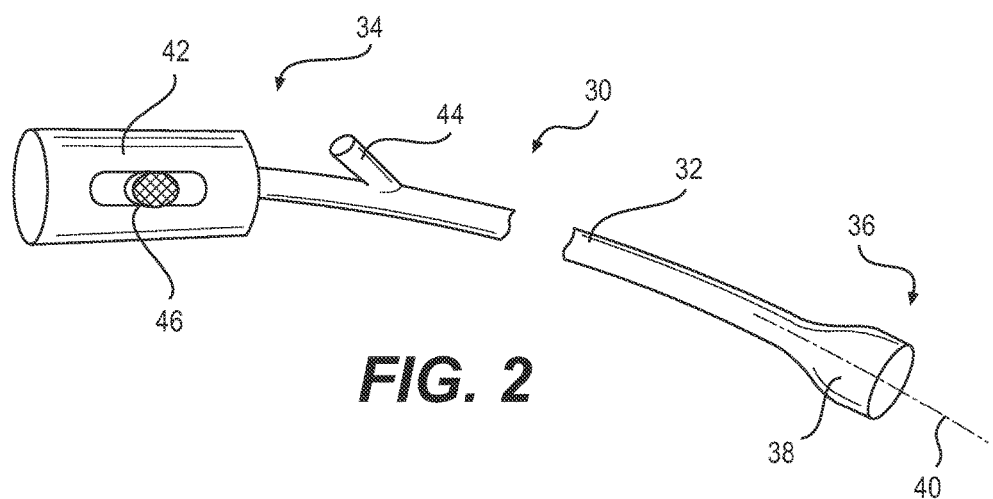
FIG. 2 illustrates an exemplary suction tool of the current disclosure.

FIG. 2 illustrates an exemplary suction tool 30. Suction tool 30 may include an elongate conduit 32 that extends from a proximal end 34 to a distal end 36 along a longitudinal axis 40. The distal end 36 of the conduit 34 may include an expandable suction head 38 and the proximal end 34 may include a handle 42. Conduit 32 may also include a port 44 that is adapted to be coupled to a vacuum source (house vacuum, vacuum pump, etc.) to provide suction at the distal end 36 of the conduit 32. Although not illustrated, port 44 may include a luer fitting to make a leak-free connection to the vacuum source. Conduit 32 may be made of a flexible material (for example, a polymeric tube), a rigid material, or a combination of both flexible and rigid materials. In some embodiments, conduit 32 may be braided or wound with plastic or metal fibers to improve conduit's resistance against kink-formation or against collapse under vacuum pressure. In some embodiments, conduit 32 may include coatings on its inside or outside surface for various purposes, for example, for protection against corrosion and/or by body fluids. In general, conduit 32 may have any dimension suitable for its intended use. In some embodiments, an elongated polymeric or polypropylene tube may serve as conduit 32.

In some embodiments, as illustrated in FIG. 2, suction head 38 and conduit 32 may be formed as a single part (that is, integrally formed). In other embodiments, a separate (or discrete) suction head 38 may be attached to the distal end 36 of the conduit 32. The suction head 38 may be attached to the conduit 32 by any known method (interference fit, adhesives, etc.). Suction head 38 may be configured to transform from a contracted configuration to an expanded configuration. In the expanded configuration, the suction head 38 may have a larger diameter and/or cross-sectional area (in a plane normal to the longitudinal axis 40) compared to its diameter and/or cross-sectional area in the contracted configuration. The suction head 38 may extend through the lumen of the ureteroscope 10 (or another lumen) in a contracted configuration, and transform to its expanded configuration when it extends out of the lumen. In some embodiments, the suction head 38 may be activated to its expanded configuration after the suction head 38 exits the lumen.

Figure 3A:
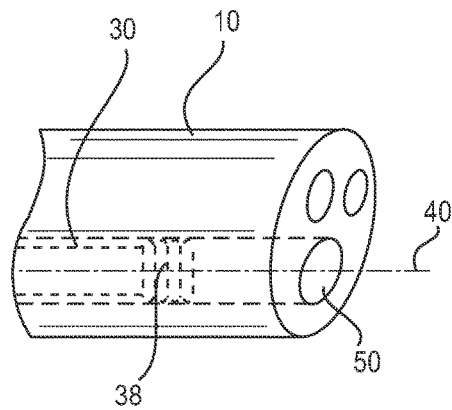
FIG. 3A illustrates an the suction head of FIG. 2 in an exemplary contracted configuration.
Figure 3B:
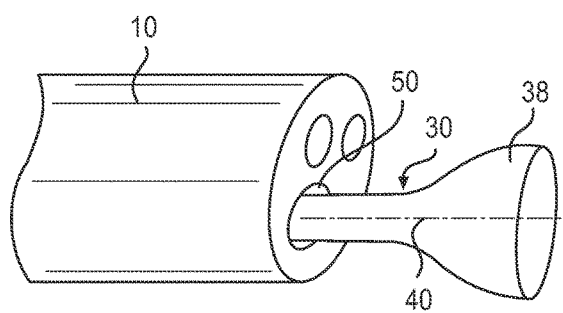
FIG. 3B illustrates an the suction head of FIG. 2 in an exemplary expanded configuration.

FIGS. 3A and 3B illustrate exemplary contracted and expanded configurations of the suction head 38. FIG. 3A illustrates the suction head 38 in its contracted configuration within a lumen 50 of ureteroscope 10, and FIG. 3B illustrates the suction head 38 in its expanded configuration outside the lumen 50. Although lumen 50 is described as a lumen of ureteroscope 10, it should be noted that, in general, lumen 50 may be a lumen of any device (catheter, sleeve, etc.). In some embodiments, the suction head 38 may be a self-expanding structure (or may include a self-expanding structure) configured to automatically transform from the contracted configuration to the expanded configuration when the suction head 38 extends from the lumen 50. In some embodiments, the suction head 38 may transform from its contracted to its expanded configuration when it is activated. The suction head 38 may be activated in any manner. In some embodiments, an activation mechanism may be provided in the handle 42 of the suction tool 30 to activate the suction head 38. The activation mechanism may include a knob 46 that may be controlled to activate the suction head 38. In some embodiments, translation or rotation of the knob 46 may provide the energy (heat, current, etc.) required to activate the suction head 38. In some embodiments, mechanical connections (wires, links, etc.) between the knob 46 and the suction head 38 may transform the suction head 38 between the contracted and expanded configurations.

In some embodiments, suction head 38 may include a shape-memory material. Any known shape-memory material (nickel titanium alloys (Nitinol), copper-aluminum-nickel alloys, shape-memory polymers, etc.) may be used to form suction head 38. As is known in the art, shape-memory materials may have a shape-memory effect and a pseudo-elastic effect. Because of the shape-memory effect, a shape-memory material may undergo deformation and remain in its deformed state until heat (or some other form of energy) is applied to it. When heat is applied, the shape-memory material may recover its original undeformed shape. Because of the pseudo-elastic effect, the shape-memory material may undergo large deformations upon the application of force and recover its original shape when the force is removed.

Figure 4A:
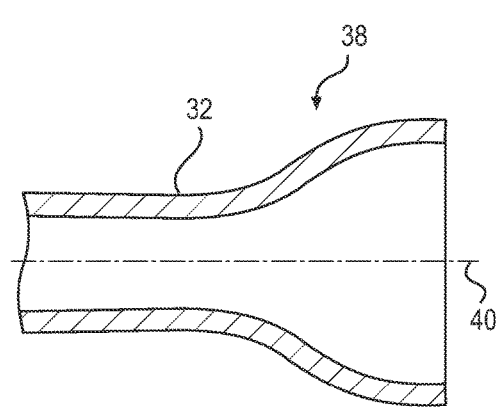
FIGS. 4A-4C illustrate exemplary embodiments of the suction head of the suction tool of FIG. 2.
Figure 4B:
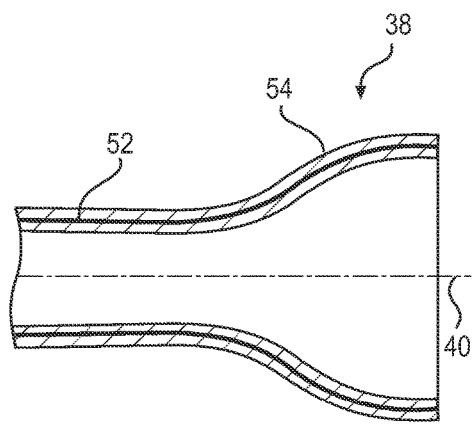
Figure 4C:
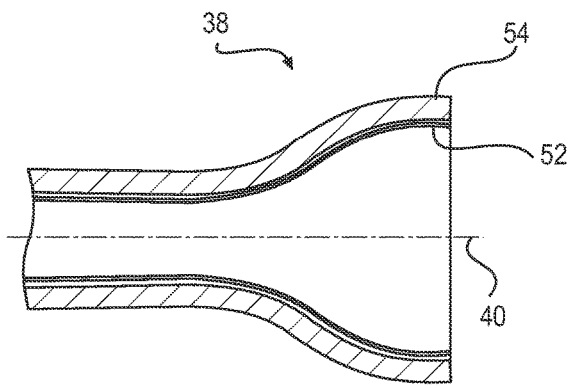

In some embodiments, as illustrated in FIG. 4A, the suction head 38 may be formed of a shape-memory material. For example, in some embodiments, the walls of the suction head 38 may be formed of a wire mesh (or a weave) of a shape-memory material. In some embodiments, the mesh may be coated with another material (for example, a polymeric material) to close the gaps between the wires. In some embodiments, as illustrated in FIGS. 4B and 4C, the suction head 38 may include material segments 52 positioned in a matrix material 54. The matrix material 54 may be the same material as the conduit 32 or a different material. The material segments 52 may include components (wires, strands, mesh, etc.) of any shape and size. In some embodiments, material segments 52 may be made of a shape-memory material. The material segments 52 may be configured to transform the suction head 38 to its expanded configuration when these elements 52 return to their undeformed configuration. In some embodiments, as illustrated in FIG. 4B, these material segments 52 may be embedded in the matrix material 54. In other embodiments, as illustrated in FIG. 4C, the material segments 52 may form a scaffolding inside or outside the matrix material 54. In some embodiments, some or all of the materials of suction head may be transparent or translucent for better visualization. In some embodiments, these materials may be soft and compliant to not cause trauma to the treated area.

When the suction head 38 is positioned in the lumen 50, the material segments 52 may be in their deformed state, and the suction head 38 may be in its contracted configuration. Extending the suction head 38 out of the lumen 50 may allow the material segments 52 to return to their undeformed shape and transform the suction head 38 to its expanded configuration. In such embodiments, the walls of the lumen may apply an inward constraining force to retain the suction head 38 in its contracted configuration within the lumen. Extending the suction head 38 out of the lumen may release the constraining force and transform the suction head 38 to its expanded configuration. In some embodiments, the material segments 52 may return to their undeformed state, and transform the suction head 38 to its expanded configuration, upon the application of heat. In some embodiments, activation (rotating, translating, etc.) of knob 46 on the handle 42 may provide the direct to the suction head 38 to transform the suction head from its contracted to its expanded configuration. For example, in some embodiments, knob 46 may activate a heater that heats material segments 52 of a suction head 38. In some embodiments, an air or a saline bladder may be operatively coupled with the suction head 38. This bladder may expand the suction head 38 when filled with air or saline.

In some embodiments, the suction tool 30 may include a sleeve. In such embodiments, the suction tool 30 may be inserted into the sleeve and the sleeve may be introduced to the ureter 16 through the lumen 50. The suction head 38 may be in its contracted configuration within the sleeve. Retracting the sleeve (that is moving the sleeve in the proximal direction with respect to the suction tool 30) may remove the constraining force of the sleeve from the suction head 38 and transform the suction head 38 to its expanded configuration.

The suction head 38 may have any size and shape. In general, the suction head 38 may have an enlarged shape. In some embodiments, the cross-sectional shape (in a plane perpendicular to the longitudinal axis 40) of the suction head 38 may be circular. However, this is not a requirement. It is contemplated that in some embodiments, the cross-section shape may be square, rectangular, elliptical, or polygonal. As illustrated in FIGS. 4A-4C, in some embodiments, the suction head 38 may have a wine glass shape (in the plane of the paper). In such embodiments, the cross-sectional area (in a plane perpendicular to the longitudinal axis 40) of the suction head 38 may decrease from its distal-most end towards the proximal direction. FIGS. 5A-5D illustrate some other exemplary shapes of suction heads 138-438. In some embodiments, as illustrated in FIG. 5A, the suction head 138 may have a substantially tubular (or cylindrical) shape. In some embodiments, a filter 60 may be provided in the suction head 138. The filter 60 may prevent (or reduce) stone fragments 70 from entering the conduit 32 and thereby prevent (or reduce) clogging of the suction tool 30. Smaller stone fragments that enter the conduit 32 through the filter 60 may be collected at the proximal end. In some embodiments, as illustrated in FIG. 5B, suction head 238 may have a substantially conical shape. In some embodiments, as illustrated in FIG. 5C, suction head 338 may have a substantially hemispherical shape. In some embodiments, as illustrated in FIG. 5D, suction head 438 may have an offset shape that is configured to prevent blocking a camera 58 or a light source at the distal end of the ureteroscope 10.

Figure 6:
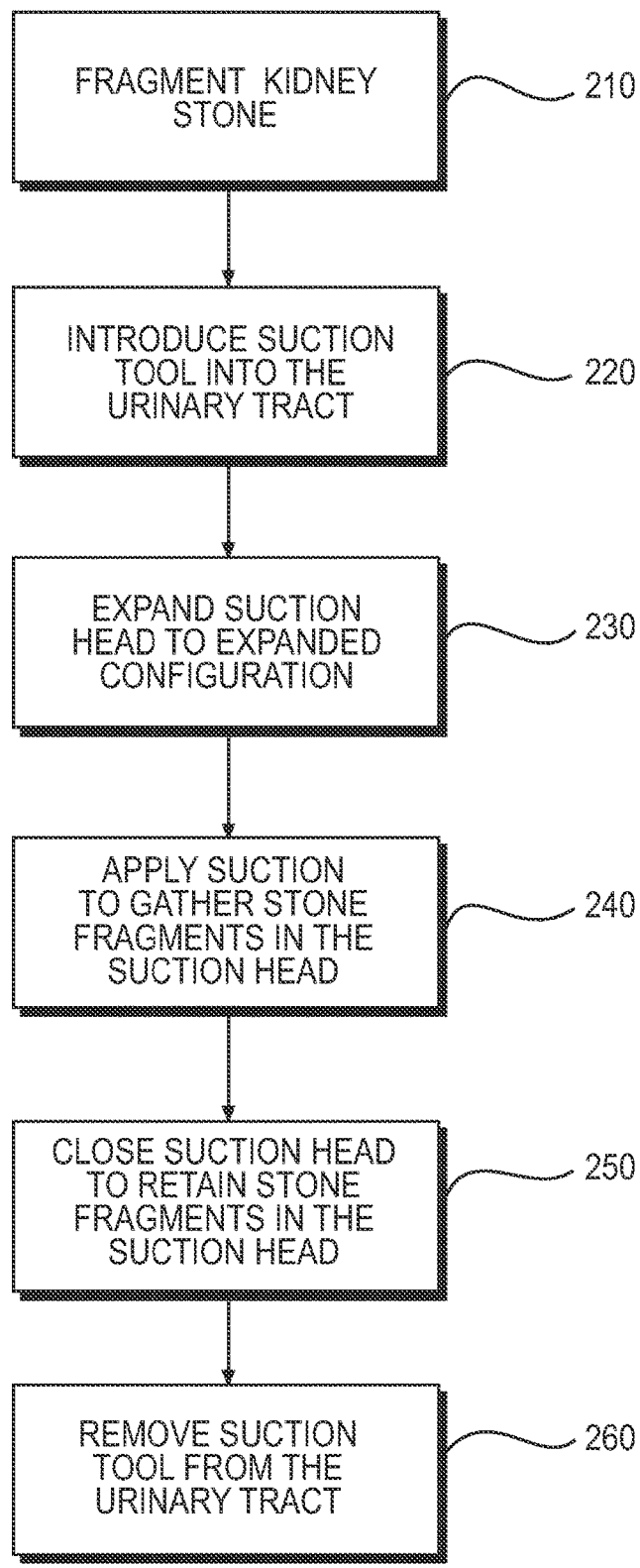
FIG. 6 is a flow chart that illustrates an exemplary method of using the suction tool of FIG. 2.

FIG. 6 is a flow chart that illustrates an exemplary method of using suction tool 30 to remove a kidney stone 20 from the urinary tract 100 of a patient. In the discussion below, reference will be made to FIGS. 1, 3A, and 3B in addition to FIG. 6. If the stone 20 is too large to be removed as one piece, the stone 20 may be fragmented or broken to smaller pieces using any known technique (step 210). The suction tool 30 may be introduced into the urinary tract 100 and positioned proximate the location of the stone fragments 70 (step 220). The suction tool 30 may be directed into the urinary tract 100 through a lumen 50 of ureteroscope 10 or through a lumen of another device. The suction head 38 of the suction tool 30 may be in its contracted configuration within lumen 50. Outside the lumen, the suction head 38 may transform to its extended configuration (step 230). In embodiments of suction tool 30 with a self-expanding suction head 38, the suction head 38 may transform to its expanded configuration automatically when it exits from the lumen 50. In some embodiments, some form of energy (heat, current, etc.) may be directed to the suction head 38 to transform the suction head 38 from the contracted to the expanded configuration. The stone fragments 70 may be collected in the suction head 38 using suction (step 240). In some embodiments, the ureteroscope 10 or the suction tool 30 may be maneuvered to move the suction head 38 in the urinary tract 100 and collect stone fragments that have shifted.

After the stone fragments 70 are collected in the suction head 38, the suction head 38 may be closed to prevent (or minimize) the escape of these stone fragments back into the urinary tract 100 (step 250). In some embodiments, the suction head 38 may be closed by pulling the suction tool 30 in a proximal direction. When the suction tool 30 is pulled in the proximal direction, the suction head 38 at least partially retracts into the lumen 50 and the suction head 38 moves towards its contracted configuration. In some embodiments, the closed configuration of a suction head 38 is the same as its contracted configuration. However, it should be noted that based on the volume and size of the stone fragments 70 in the suction head 38, in some embodiments, the closed configuration of the suction head 30 may not be the same as its contracted configuration. In such cases, when pulled in the proximal direction, the suction head 38 may not retract completely into the lumen 50. Instead, a portion of the suction head 38 may remain outside the lumen 50 with the walls of the suction head 38 forced towards the longitudinal axis 40 by the inner walls of the lumen 50. In general, the closed configuration of a suction head 38 may be a configuration that is between its contracted and expanded configurations. In the closed configuration, the stone fragments 70 may be tightly held between the walls of the suction head 38 or may be enclosed by the walls.

The suction tool 30 with the stone fragments may then be withdrawn from the urinary tract 100 (step 260). In some embodiments, the suction tool 30 may be withdrawn from the urinary tract 100 through the lumen 50 of the ureteroscope 10. In some embodiments, the suction tool 30 along with the ureteroscope 10 may be withdrawn from the urinary tract 100 together. It should be noted that the method of FIG. 6 is only exemplary and that many variations can be made to the illustrated method. For instance, in some embodiments, the fragmenting step (step 210) may be eliminated and the suction tool 30 may be used to remove an unfragmented stone from the body.

Using the exemplary devices and methods described herein, a medical professional may readily and accurately remove kidney stones from a patient's body. It is understood, however, that while embodiments of the present disclosure have been described with reference to removing kidney stones from the urinary tract, the teachings of the present disclosure may be used to remove material from any lumen of the body. Further, the devices herein may be single-use which can be discarded after one use or may be used again after sterilization.

Other embodiments of the present disclosure will be apparent to those skilled in the art after consideration of the specification and practice of the embodiments disclosed herein. It is intended that the specification and examples be considered as exemplary only, with a true scope and spirit of the disclosure being indicated by the following claims.

I claim:

1. An endoscopic suction device, comprising:
   a conduit extending from a proximal end to a distal end along a longitudinal axis, the proximal end configured to be coupled to a vacuum source and the distal end configured to extend into a subject's body;
   an expandable suction head at the distal end of the conduit, the suction head being configured to expand from a contracted configuration to an expanded configuration within the body in response to the application of heat or current, and
   a filter positioned transverse to the longitudinal axis, wherein the filter is positioned in a proximal portion of the expandable suction head, a distal portion of the conduit, or both the proximal portion of the expandable suction head and the distal portion of the conduit, and wherein the filter spans a cross-sectional area of the endoscopic suction device to prevent material from entering the conduit.

2. The device of claim 1, wherein the distal end of the conduit is sized to extend into the body through a lumen of a medical device, and wherein the suction head is configured to transform from a contracted configuration within the lumen to an expanded configuration outside the lumen.

3. The device of claim 2, wherein the lumen is a lumen of an ureteroscope.

4. The device of claim 1, further including an activation device configured to apply the heat or current to the suction head to transform the suction head from the contracted configuration to the expanded configuration.

5. The device of claim 1, wherein, in the expanded configuration, a cross-sectional area of the suction head transverse to the longitudinal axis decreases from a distalmost end of the suction head to a proximal end of the suction head.

6. The device of claim 1, wherein a cross-sectional area of the suction head transverse to the longitudinal axis is greater in the expanded configuration than in the contracted configuration, and
   wherein the suction head includes a distal portion, and wherein, in the expanded configuration, the distal portion extends parallel to the conduit, the proximal portion extends at an angle to the conduit, and a longitudinal length of the distal portion is greater than a longitudinal length of the proximal portion.

7. The device of claim 1, wherein the conduit and the suction head are formed as a single part.

8. The device of claim 1, wherein the suction head is configured to contract from the expanded configuration to the contracted configuration in response to the removal of the applied heat or current.

9. A method of using a suction device to remove an object from a subject's body, the suction device including an expandable suction head at a distal end of a conduit, wherein the conduit extends from a proximal end to a distal end along a longitudinal axis, the proximal end configured to be coupled to a vacuum source and the distal end configured to extend into a subject's body, wherein the expandable suction head includes a shape-memory alloy and is configured to expand from a contracted configuration to an expanded configuration within the body when extended outside of a lumen of a medical device, and further including a filter positioned at a junction between a proximal end of the suction head with the distal end of the conduit,
the method comprising:
extending the suction device into the body through a lumen of a medical device;
expanding the suction head from a contracted configuration to an expanded configuration within the body by applying heat or current;
applying suction to move the object into the expanded suction head, wherein the filter prevents the object from entering the conduit; and
removing the suction device with the object from the body.

10. The method of claim 9, wherein expanding the suction head includes transforming the suction head from a contracted configuration within the lumen to an expanded configuration outside the lumen.

11. The method of claim 9, wherein removing the suction device includes removing the suction device through the lumen.

12. The method of claim 9, wherein removing the suction device includes removing the medical device along with the suction device from the body.

13. An endoscopic suction device, comprising:
a conduit extending from a proximal end to a distal end along a longitudinal axis, the proximal end configured to be coupled to a vacuum source and the distal end configured to extend into a subject's body; and
an expandable suction head at the distal end of the conduit, the suction head including a shape-memory alloy and being configured to expand from a contracted configuration to an expanded configuration within the body when extended outside of a lumen of a medical device,
wherein the expandable suction head includes a filter positioned at a junction between a proximal end of the suction head and the distal end of the conduit to prevent material from entering the conduit.

14. The device of claim 13, wherein the suction head is formed of a wire mesh of the shape-memory alloy coated with a polymeric material.

15. The device of claim 13, wherein the suction head is transparent, and wherein in the expanded configuration, the suction head forms a distally-facing hemispherical shape.

* * * * *